United States Patent [19]

Frank et al.

[11] Patent Number: 4,600,795

[45] Date of Patent: Jul. 15, 1986

[54] PREPARATION AND RECOVERY OF METHACRYLIC ACID AND ITS ESTERS

[75] Inventors: Peter J. Frank, Westerville; Jerry R. Hite, Columbus, both of Ohio

[73] Assignee: Ashland Oil, Inc., Ashland, Ky.

[21] Appl. No.: 369,383

[22] Filed: Apr. 19, 1982

[51] Int. Cl.[4] .................... C07C 51/377; C07C 51/50;
C07C 57/075; C07C 67/317; C07C 67/62;
C07C 69/54

[52] U.S. Cl. .................................... 562/599; 560/214;
560/218; 562/600

[58] Field of Search ................ 562/599, 600; 560/214, 560/218

[56] References Cited

U.S. PATENT DOCUMENTS 3,658,895  4/1972  Riemann et al. ............... 562/599
4,182,907  1/1980  Grasselli et al. ............... 562/600

FOREIGN PATENT DOCUMENTS 2438464  2/1975  Fed. Rep. of Germany ...... 562/599

*Primary Examiner*—Vivian Garner
*Attorney, Agent, or Firm*—John F. Jones

[57] ABSTRACT

In the recovery and purification of methacrylic acid or its esters produced by the vapor phase catalytic oxydehydrogenation of isobutyric acid or its esters the problem of downstream plugging is avoided by the inclusion of a small amount of surfactant in the gaseous effluent at or near the point of its condensation.

4 Claims, No Drawings

PREPARATION AND RECOVERY OF METHACRYLIC ACID AND ITS ESTERS

This invention relates to the recovery of methacrylic acid or ester thereof from the vapor phase catalytic oxydehydrogenation of isobutyric acid or ester thereof which involves a process for adding a surfactant material to the condensed methacrylic acid or ester thereof at or near the point of condensation in the recovery area.

It is known that methacrylic acid or esters thereof can be prepared by the catalytic vapor phase oxydehydrogenation of isobutyric acid or esters thereof. U.S. Pat. No. 3,948,959, for instance, describes a gas phase oxydehydrogenation process in which $\alpha,\beta$-olefinically unsaturated acids are obtained by using an iron phosphate type of catalyst. The reaction is carried out at a temperature in the range of 100°-500° C. and the reaction products leave the reactor in gaseous form. No details are given as to how the olefinically unsaturated acid would be recovered and purified if a commercial process were involved, but it is normal to condense the gaseous effluent by cooling with or without an entraining liquid such as water. The thus condensed liquid is further treated to separate and purify the product.

It is well known that methacrylic acid and its esters are active vinyl monomers which will polymerize readily when catalyzed by various initiators and by heat itself. Thus, it is customary in the art to use polymerization inhibitors to prevent premature polymerization of these materials in their recovery, purification and storage. Polymerization inhibitors are not always effective, particularly when present in methacrylic acid or esters which are in or near the gaseous phase as they are in the oxydehydrogenation process. As a result, some premature polymerization of these materials often occurs as they are condensed from the oxydehydrogenation effluent and this polymer formation ultimately causes plugging of the lines and columns in the recovery and purification portion of the commercial plant. The resulting shutdowns of the plant or units of the plant to remove polymer plugs is costly and time consuming. One suggested solution to this problem is to heat the inner surface of the pipes which connect the oxidation reactor with the next process step to a temperature higher than the boiling point of the materials in the effluent (Japan Kokai No. 75/126,605) but this method uses additional energy and does not really solve the polymer formation which is still likely to occur further downstream in the recovery and purification process.

We have discovered that the addition of a surfactant material to the gaseous effluent from a gas phase oxidative dehydrogenation reaction producing methacrylic acid or esters thereof at or near the point of condensation of said effluent will effectively prevent plugging in the recovery and purification portion of the process for production of methacrylic acid or esters thereof.

More particularly, we have discovered that in the preparation of methacrylic acid by gas phase catalytic oxydehydrogenation of isobutyric acid, clogging of pipe lines connecting the outlet of the reactor to the next process apparatus is prevented by introducing a non-ionic, anionic or cationic surfactant to the gaseous effluent from the reactor at or near the point of condensation of said effluent.

We have found that normal prolonged operation of an oxydehydrogenation reactor will result in pipe line plugging downstream of the oxydehydrogenation reactor. Attempts to prevent this downstream plugging by us by including a polymerization inhibitor into the downstream piping to prevent clogging have failed. We have discovered, however, that the use of surfactant dispersing agents for this purpose will prevent the plugging which otherwise occurs.

The oxydehydrogenation of isobutyric acid to methacrylic acid is performed in the vapor phase at high temperatures as previously indicated. In the presence of oxygen (air) and water the reaction products are condensed and the effluents collected for downstream separation and purification. It is at or near the point of condensation that one usually will notice the formation of a solid clogging material (probably polymethacrylic acid), and such clogging will continue and eventually cause plugging of the downstream piping. This will reduce the overall production of methacrylic acid and cause periodic shutdowns for cleaning of the fouled piping, valves, columns, etc.

Plugging can be prevented by the introduction of a surfactant material in the range of from 1 to 6000 ppm based on the weight of the other components in the gaseous product into the downstream portion of the reactor train at a point just prior to or at the area of effluent condensation. The only precaution to be taken in this regard is that the surfactant material should not be introduced into the recovery chain at a point in which the temperature is at or above the point of decomposition of the surfactant material. Although the exact mechanism whereby the surfactant material functions to prevent plugging in the recovery and purification chain is not known, it is believed that the surfactant is at least partially effective because it prevents adhesion to the pipe interior walls of any polymethacrylic acid which might form following the condensation of the reactor effluent. It is also possible that the surfactant prevents methacrylic acid from adhering to the pipe walls and forming polymerization sites.

As was pointed out earlier, any surfactant material can be used in our invention. Typical types of surfactants useful in our process include the alkyl sulfonates, sulfonated amines and amides, diphenyl sulfonates, ethoxylated fatty acids, lignin and lignin derivatives, olefin sulfonates, phosphate derivatives, polyamino carboxylic. acids, alkyl sufosuccinates, alcohol sulfates, ethoxylated alcohol sulfates, sulfates and sulfonates of ethyxylated alkyl phenols, sulfates of fatty esters, sulfates and sulfonates of oils and fatty acids, sulfonates of benzene, toluene and xylene, sulfonates of condensed naphthalenes, sulfonates of dodecyl and tridecylbenzenes, sulfonates of petroleum, taurates, generally surfactants of the types more fully described in *Chemical and Engineering News*, Jan. 11, 1982, pages 13–16. Particularly preferred are the non-ionic types of surfactants of the alkyl phenol ethoxylate type which can be further described as an ionically neutral compound composed of an organic hydrophobe containing, usually, adducts of ethylene oxide.

The surfactants used in the process of this invention can be used per se, in solution, or in suspension in water.

The process of this invention is further illustrated in the following Example.

EXAMPLE

A. An oxidative dehydrogenation reaction was carried out in a tubular, stainless steel, reactor $4\frac{1}{2}'$ long with an internal diameter of 0.87". The reactor contained 3/16" pellets of a ferric phosphate catalyst. The feed to the reactor was a mixture of isobutyric acid:oxygen:nitrogen:water in the molar ratio of 1:0.7:3.4:20, respectively. The reaction temperature was 380°±5° C., reactor pressure was 1.5 psig, and weight hourly space velocity was 4. The reaction produced initially 0.36 pound per hour of methacrylic acid per pound of catalyst. After some 36 hours of continuous reaction the ½" O.D., ⅜" I.D., condenser plugged with enough solid material to cause a 7-10 psig pressure drop through the reactor. This experiment is for comparison purposes and is outside the scope of this invention.

B. The procedure of A above was repeated except that a non-ionic surfactant octyl, phenoxy ethanol containing 10 mols of ethylene oxide (Triton X-100, Rohm and Haas Company) was included in 200 parts per million based on the weight of the other components in the gaseous product to a section of the condenser piping in an area where the vapor temperature was a little less than 250° C. so as to avoid thermal decomposition of the surfactant. After 650 hours of continuous operation no increase in pressure was observed in the system.

We claim:

1. In a process for the vapor phase catalytic oxydehydrogenation of isobutyric acid or its esters to form methacrylic acid or its esters wherein the gaseous product is condensed and purified, the improvement consisting of adding to the gaseous product at or about the point of its condensation from 1 to 6000 ppm of a surfactant material selected from the group consisting of an anionic a cationic and a non-ionic surfactant.

2. The process of claim 1 wherein the surfactant is a non-ionic surfactant.

3. The process of claim 2 wherein isobutyric acid is oxydehydrogenated to methacrylic acid.

4. The process of claim 3 wherein about 200 ppm of surfactant is used in the gaseous product.

* * * * *